US005369008A

United States Patent [19]

Arlinghaus et al.

[11] Patent Number: 5,369,008
[45] Date of Patent: Nov. 29, 1994

[54] METHODS FOR THE DETECTION OF BCR-ABL AND ABNORMAL ABL PROTEINS IN LEUKEMIA PATIENTS

[75] Inventors: Ralph B. Arlinghaus, Bellaire, Tex.; Jean Y. J. Wang, San Diego, Calif.; Jie O. Guo, Houston, Tex.

[73] Assignee: Board of Regents, The University of Texas System, Austin, Tex.

[21] Appl. No.: 152,069

[22] Filed: Nov. 12, 1993

Related U.S. Application Data

[63] Continuation of Ser. No. 704,981, May 24, 1991, abandoned.

[51] Int. Cl.$^5$ ............... G01N 33/573; G01N 33/574; G01N 33/53
[52] U.S. Cl. .................. 435/7.23; 435/15; 435/183; 435/184; 435/814; 436/514; 436/63; 436/64; 436/813; 530/388.8; 530/388.85
[58] Field of Search .............. 435/7.23, 15, 183, 184, 435/814; 436/514, 63, 64, 813; 204/182.8; 530/388.8, 388.85

[56] References Cited

U.S. PATENT DOCUMENTS 4,939,083  7/1990  Fukuda et al. .................. 435/7.23

OTHER PUBLICATIONS

Maxwell et al., "Philadelphia Chromosome-positive Cells from Chronic Myelogenous Leukemia Patient," *Cancer Res*, 47, 1731–1739, 1987.
Schiff–Maker, et al., Journal of Virology, vol. 57, No. 3, pp. 1182–1186, 1986.
Konopka, J. B., et al., Journal of Virology, vol. 51, No. 1, pp. 223–232, 1984.
Heisterkamp et al., Localization of the c–abl oncogene adjacent to a translocation break point in chronic myelocytic leukaemia. Nature 306:239–242 (1983).
Groffen et al., Philadelphia chromosomal breakpoints are clustered within a limited region, bcr, on chromosome 22. Cell 36:93–99 (1984).

Wang et al., The mouse c–abl locus: molecular cloning and characterization. Cell 36:349–356 (1984).
Konopka et al., An alteration of the human c–abl protein in K562 leukemia cells unmasks associated tyrosine kinase activity, Cell 37:1035–1042 (1984).
Gale and Canaani, An 8–kilobase abl RNA transcript in chronic myelogenous leukemia. Proc. Natl. Acad. Sci. USA 81:5648–5652 (1984).
Wang and Baltimore, Localization of tyrosine kinase–coding region in v–abl oncogene by the expression of v–abl–encoded proteins in bacteria. J. Biol. Chem. 260(1):64–71 (1985).
Kloetzer et al., The human cellular abl gene product in the chronic myelogenous leukemia cell line K562 has an associated tyrosine protein kinase activity. Virology 140:230–238 (1985).
Wang, J., Isolation of antibodies for phosphotyrosine by immunization with a v–abl oncogene–encoded protein. Mol. Cell. Biol. 5(12):3640–3643 (1985).
Kurzrock et al., A novel c–abl protein product in Philadelphia–positive acute lymphoblastic leukaemia. Nature 325:631–635 (1987).

(List continued on next page.)

*Primary Examiner*—Toni R. Scheiner
*Attorney, Agent, or Firm*—Campbell and Flores

[57] ABSTRACT

The present invention provides methods for detecting and quantitating BCR-ABL gene products and other abnormal ABL gene products of Ph$^1$-positive leukemic cells. The invention further provides methods for determining the relative number of leukemic cells compared with normal ABL cells to assess the tumor burden of a patient. In another aspect, the methods of the present invention can be used to determine a specific phase of leukemia, particularly chronic-phase CML.

32 Claims, 7 Drawing Sheets

OTHER PUBLICATIONS

Chan et al., A novel abl protein expressed in Philadelphia chromosome positive acute lymphoblastic leukaemia. Nature 325:635–637 (1987).

Walter et al., Novel chimaeric protein expressed in Philadelphia positive acute lymphoblastic leukaemia. Nature 329:851–853 (1987).

Hermans et al., Unique fusion of bcr and c-abl genes in Philadelphia chromosome positive acute lymphoblastic leukemia. Cell 51:33–40 (1987).

Maxwell et al., Analysis of $P210^{bcr-abl}$ tyrosine protein kinase activity in various subtypes of Philadelphia chromsome-positive cells from chronic myelogenous leukemia patients. Cancer Res. 47:1731–1739 (1987).

Kipreos et al., Isolation of temperature-sensitive tyrosine kinase mutants of v-abl oncogene by screening with antibodies for phosphotyrosine. Proc. Natl. Acad. Sci. USA 84:1345–1349 (1987).

Clark et al., Expression of a distinctive bcr-abl oncogene in $Ph^1$-positive acute lymphocytic leukemia (ALL). Science 239:775–777 (1988).

Gutkind and Robbins, Translocation of the FGR protein-tyrosine kinase as a consequence of neutrophil activation. Proc. Natl. Acad. Sci. USA 86:8783–8787 (1989).

METHODS FOR THE DETECTION OF BCR-ABL AND ABNORMAL ABL PROTEINS IN LEUKEMIA PATIENTS

This invention was made with Government support under Grant No. PCM83-14300 awarded by the National Science Foundation and Grant Nos. R01-CA-47372 and P01-CA-49639 awarded by the National Institute of Health. The Government has certain rights in this invention.

This application is a continuation of application U.S. Ser. No. 07/704,981, filed May 24, 1991, now abandoned, the contents of which are hereby incorporated by reference into the present disclosure.

BACKGROUND OF THE INVENTION

More than 95% of patients with chronic myelogenous leukemia (CML) possess the Philadelphia chromosome ($Ph^1$), an abnormal chromosome present in leukemia cells that originates from the reciprocal translocation between chromosomes 9 and 22. This chromosomal exchange joins the 5' two-thirds of the BCR gene remaining on chromosome 22 to a large portion of the ABL gene translocated from chromosome 9. The BCR gene is described in more detail in Groffen et al., *Cell* 36:93 (1984), while the ABL gene is described in Heisterkamp et al., *Nature* 306:239 (1983) and in Gale & Canaani, *PNAS (U.S.A.)* 81:5648 (1984).

The fused genes generate a hybrid mRNA with a continuous open reading that encodes a BCR-ABL protein of more than 2,000 amino acids. Two types of BCR-ABL transcripts have been detected which differ by a small coding exon originally termed the 3' bcr exon within the breakpoint cluster region of the BCR gene. These two transcripts encode two BCR-ABL proteins of 2023 and 1999 amino acids, depending upon whether the 3' bcr exon is present in the hybrid mRNA. These proteins migrate in sodium dodecyl sulfate (SDS) polyacrylamide gels with an estimated size of 210,000 daltons and are termed P210 BCR-ABL.

The $Ph^1$ is also present in some patients with acute lymphocytic leukemia (ALL) and acute myelogenous leukemia (AML). $Ph^1$-positive ALL patients express either the typical P210 BCR-ABL protein or a smaller protein termed P185 BCR-ABL. The latter results from a more 5' break in the BCR gene within a large intron between exons 1 and 2.

Both the CML and ALL forms of the BCR-ABL protein possess an activated tyrosine kinase activity. The assay for the BCR-ABL tyrosine kinase activity is widely used as a means to detect the BCR-ABL protein in cell lines derived from blast crisis CML patients and is described in Maxwell et al, *Cancer Res.* 47:1731 (1987). The BCR-ABL protein kinase assay has also been used to detect P210 BCR-ABL in uncultured cells from patients in blast crisis as reported in Maxwell et al., supra. Although the BCR-ABL protein can be routinely detected in blood cells from blast crisis CML patients by assaying for its activated tyrosine kinase activity, detection of P210 BCR-ABL in early-stage CML patients (chronic phase) has not yet been possible according to Maxwell et al. Attempts to detect the BCR-ABL protein in chronic-phase patients by this assay have been hindered by large numbers of mature cells in blood and bone marrow samples in these patients.

According to published reports, the patient samples contain high concentrations of degradative enzymes. The tyrosine kinase activity, which is detected in blast crisis cell samples that contain more than 50% blast cells, is rarely detected in samples from chronic-and accelerated-phase patients. The extracts of mature granulocytes, either from normal or CML patients, rapidly destroy P210 kinase activity from extracts of $Ph^1$-positive cultured cells according to experiment described in Maxwell et al., supra.

The degradative factors in mature white blood cell populations must be inhibited before the tyrosine kinase assay of BCR-ABL proteins can be used to monitor patients for the presence of leukemic cell clones. This inhibition has not yet been possible to achieve.

Thus, a need exists for an assay that can detect and quantitate $Ph^1$-positive leukemic cell proteins. Such assays would be useful for diagnosing and monitoring patients in the early phases of CML and other types of leukemia. The present invention satisfies this need and provides related advantages as well.

SUMMARY OF THE INVENTION

The present invention generally relates to detecting $Ph^1$-positive leukemic cells expressing BCR-ABL and other abnormal ABL gene products. More specifically, the present invention provides methods for detecting the presence or absence of BCR-ABL gene products and abnormal ABL gene products in samples from patients with leukemia, particularly chronic phase CML.

Methods for determining the amounts or levels of such gene products are also provided in the present invention. In addition, the present invention further relates to determining the number of leukemic cells in a sample relative to the number of normal white cells by determining the ratio of abnormal ABL proteins to normal ABL proteins in the sample. These ratios can be used to determine the tumor burden in a patient or to stage the disease into a particular phase.

The methods of the present invention use antibodies specific to ABL proteins, particularly antibodies that recognize an epitope within the SH2 region of a normal ABL protein. Accordingly, the present invention also provides pure epitopes within this region of the ABL protein.

Finally, kits for performing the methods of the present invention are also provided. The kits contain anti-ABL antibodies and useful ancillary reagents.

DETAILED DESCRIPTION OF THE INVENTION

The present invention generally relates to the use of BCR-ABL and abnormal ABL cytoplasmic proteins as markers of malignancy in certain leukemic blood cells. The BCR-ABL and abnormal ABL proteins can be used, for example, as markers of chronic myelogenous leukemia (CML), acute myelogenous leukemia (AML) and acute lymphocytic leukemia (ALL). The present invention advantageously provides methods that are relatively simple and convenient to detect or quantitate BCR-ABL and abnormal ABL proteins associated with Ph[1]-positive leukemic cells. These in vitro methods also provide a safe means to evaluate a patient having a disorder associated with such leukemic cells.

More specifically, the present invention provides methods for detecting the presence or absence of a BCR-ABL or abnormal ABL gene product in a patient sample using antibodies reactive with these gene products. Such methods include the steps of (a) denaturing degradative enzymes in the sample; (b) contacting the sample with an antibody reactive with the BCR-ABL and abnormal ABL gene products, but not cross-reactive with other non-ABL components in the sample; and (c) determining the binding of the antibody to the sample, in which antibody binding to the sample indicates the presence of the BCR-ABL or abnormal ABL gene product.

The detection of BCR-ABL and abnormal ABL gene products using the above methods can in turn be correlated with the diagnosis of a disorder associated with Ph[1]-positive leukemic cells since BCR-ABL and abnormal ABL gene products are known to be diagnostic markers of CML. BCR-ABL gene products having apparent molecular weights of about 210 kDa (P210 or P210 BCR-ABL) are particularly useful for the diagnosis of chronic-phase CML patients using the methods of the present invention. Other abnormal ABL gene products, particularly abnormal ABL gene products having molecular weights of about 185 kDa (P185) and 190 kDa (P190), can also be used to detect chronic-phase leukemia patients.

As used herein, the term "abnormal ABL gene product" refers to an ABL gene product that is not of the normal ABL protein molecular weight size of about 145 kDa. Generally, abnormal ABL gene products associated with Ph[1]-positive leukemic cells have a higher molecular weight compared with the normal ABL gene product. In addition, the terms "gene product" and "protein" are used interchangeably herein when referring to a product encoded by a BCR-ABL or an ABL gene.

For example, using the methods of the present invention, it was discovered that many chronic-phase CML patients have one or two proteins of about 190-kDa in addition to P210 BCR-ABL. It is believed that these are BCR-ABL proteins and, based upon previous experience, they could be degradation products of P210 BCR-ABL, or may represent some altered form of the BCR-ABL protein. One patient in the studies detailed in Example V, lacked detectable P210 BCR-ABL and contained only the 190-kDa abnormal size ABL protein. These samples also contained P145 ABL of the normal size.

Another altered form of the BCR-ABL protein (P185) has been observed in the case of some Ph[1]-positive ALL patients. The P185 protein is encoded by RNA that joins the first bcr exon to the second exon of the ABL gene. Two Ph[1]-positive ALL patients with BCR-ABL transcripts that encode a P190 BCR-ABL protein with yet a different structure were recently reported. The structure of these latter RNAs joins the 3' bcr exon to abl exon 3.

The present invention further provides methods for the quantitative determination of a BCR-ABL gene product, an abnormal ABL gene product or a normal ABL gene product in a patient sample. These methods involve (a) denaturing degradative enzymes in the sample; (b) contacting the sample with an antibody reactive with the BCR-ABL and abnormal ABL gene products, but not cross-reactive with non-ABL components in the sample; and (c) determining the amount of antibody binding to the BCR-ABL gene product, abnormal ABL gene product or normal ABL gene product, in which the amount of antibody binding to the BCR-ABL gene product, abnormal ABL gene product or normal ABL gene product indicates the quantity of the BCR-ABL gene product, abnormal ABL gene product or normal ABL gene product, respectively, in the sample.

The present invention also provides methods for determining the tumor burden of a patient by evaluating the relative amount of leukemic cells in a sample compared with normal white blood cells. Such methods include the steps of (a) denaturing any degradative enzymes in the sample; (b) contacting the sample with an antibody having reactivity with a BCR-ABL, abnormal ABL and normal ABL gene products, but not cross-reactive with other non-ABL components in the sample; and (c) determining the amount of antibody binding to the BCR-ABL gene product, abnormal ABL gene product and normal ABL gene product. The amount of antibody binding to each gene product relates to the amount of each gene product in the sample.

The resulting amounts of each gene product can be used to determine the ratio of BCR-ABL and/or abnormal gene products to normal ABL gene products. The ratio correlates with the relative amount of leukemic cells in the sample compared with normal white blood cells. Therefore, the ratio can be used to determine the tumor burden in a patient.

The quantitative measurement of BCR-ABL and abnormal ABL proteins can also be used to monitor or stage CML patients throughout the progression of a Ph[1]-positive disease. Generally, a ratio of about 0.5 to about 2.3 relates to the chronic phase, while a ratio in the range of about 2.5 or greater relates to the blast crisis phase. Thus, an elevated ratio of Ph[1]-associated proteins of more than about 2.5 fold is indicative of the serious blast crisis phase. These measurements can be used to determine the appropriate therapy for a particular phase of the disease. As known to those skilled in the art, there are several advantages and therapeutic modalities available when the disease is detected in the early chronic phase compared with the late blast crisis phase. Thus, the prognosis of a CML patient can also be correlated with the amount of BCR-ABL or abnormal ABL proteins in a sample and the corresponding leukemic cell burden of a patient.

For use in the methods of the present invention, a sample can be obtained from various physiological sources in a patient, including whole blood, bone marrow, plasma, or a solid tumor from the spinal cord, for example. Solid tumors can be disrupted by any means known in the art such as by homogenization, for example, prior to analysis. A sample can also include any prepared fluid to be analyzed for the presence or concentration of the BCR-ABL, abnormal ABL or normal ABL proteins for use as controls, calibers and other various purposes for which a solution containing such proteins is desired.

Various procedures that distinguish among proteins of different molecular weight or other physical properties differentiating normal from abnormal ABL proteins, including BCR-ABL proteins, can be used. However, Western blotting is particularly useful for the methods of the present invention since it is relatively simple and convenient, yet highly sensitive in differentiating proteins of varying molecular weight.

Prior to analyzing a sample in Western blotting, the sample can be optionally pretreated with an enzyme inhibitor. As discussed previously, samples obtained from a patient may contain enzymes that are believed to degrade the cytoplasmic proteins to be analyzed. Such degradative enzymes include, for example, proteases and phosphatases. These degradative enzymes can be at least partially degraded or inactivated prior to further treatment to complete the inactivation of these enzymes.

Accordingly, an effective amount of an enzyme inhibitor can be added to the sample to assist in the inactivation of any degradative enzymes present in the sample. Protease inhibitors, such as trasylol, phenylmethylsulfonyl fluoride, benzamidine, diisopropylfluorophosphate (DIFP), leupeptin, pepstatin, EDTA, EGTA, and the like, or any combination of these compounds can partially degrade or inactivate such enzymes.

Even if the sample is pretreated with an enzyme inhibitor, it is subjected to further treatment to completely denature such enzymes without degrading the peptide bonds of the proteins to be assayed. For instance, the sample is heated to a temperature that effectively denatures the enzymes but does not significantly break the peptide bonds of the BCR-ABL proteins. One skilled in the art will know that such pretreatment of the sample will not be necessary for samples that do not contain degradative enzymes. Preferably, the sample contains about $10^6$ to $10^7$ cells that are added to a 1% w/v sodium dodecyl sulfate (SDS) sample buffer containing about 10% v/v 2-mercaptoethanol (2-MEO) and placed in a boiling water bath for about 5-7 minutes. Other reagents that disrupt the disulfide bond of the enzymes can be substituted for 2-MEO, such as, dithiothreitol (DTT). These conditions are also sufficient to lyse the cells.

After standard electrophoresis, the lysate is then blotted or immobilized onto a suitable substrate, such as cellulose nitrate filters, prior to adding antibody. The anti-ABL antibody is then contacted with the immobilized proteins. The term "contacting" encompasses any means by which the antibody comes into close physical proximity to the proteins sufficient for the antibody to bind to BCR-ABL proteins and other abnormal and normal ABL proteins present in the sample. In addition, one skilled in the art will readily know the meaning of the term "contacting". For example, such contact can be accomplished by pouring an antibody solution onto the blotted proteins or by dipping the immobilized proteins into an antibody solution followed by a period of incubation.

The term "antibody" as used herein means a polyclonal or a monoclonal antibody or a fragment thereof reactive with the BCR-ABL and abnormal ABL gene products, but not cross-reactive with other non-ABL proteins or components in the sample to be analyzed. Antibodies that are also reactive with normal ABL proteins can be used in the present methods, particularly in determining the ratio of BCR-ABL or abnormal ABL proteins to normal white blood cell proteins. The antibodies useful in the present invention can be produced by any method known in the art, including biologically or synthetically produced antibodies.

Recombinantly-produced antibody-like products are also within the definition of an "antibody" as used herein. Methods for producing such products are described, for example, in Skera & Pluckthun, *Science*, 240:1038-1040 (1988), which is incorporated herein by reference.

Immunogens useful for producing polyclonal or monoclonal antibodies can be a normal or abnormal ABL protein or a fragment of the protein. Alternatively, the immunogen can be chemically synthesized from the entire or partial amino acid sequence of the normal ABL protein identified in Wang et al., *Cell* 36:349-356 (1984), which is incorporated herein by reference. In addition, fusion proteins such as t-ABL or t-E-ABL, for example, can also be used as immunogens. The fusion protein, t-ABL, is identified and characterized in Wang & Baltimore, *J. Biol. Chem.* 260:64-71 (1985), while t-E-ABL is described in Kipreos et al., *PNAS (U.S.A.)* 84:1345-1349 (1987), both of which are incorporated herein by reference. Methods for producing chemically-synthesized antibodies and polypeptides are well known in the art. For example, the Merrifield solid phase method is described in Merrifield et al., *J. Am. Chem. Soc.* 35:2149-2156 (1963) and Kent et al., *Synthetic Peptides in Biology and Medicine* (Elsevier Science Publishers, 1985), both of which are incorporated herein by reference.

Polyclonal antibodies can be obtained from antisera of animals immunized with an appropriate immunogen. Methods for obtaining polyclonal antibodies are well known in the art and are described, for example, in E. Harlow & D. Lane, *Antibodies: A Laboratory Manual*, 92-144 (Cold Spring Harbor Laboratory, 1988), which is incorporated herein by reference.

Similarly, various methods known in the art can be used to generate high affinity monoclonal antibodies. Such antibodies can be produced by methods according to or modified from the method described in Milstein & Kohler, *Nature* 256:495-97 (1975). Briefly, an animal is first immunized with an immunogen. The spleen cells from the immunized animal is then fused with immortalized cells to produce hybridomas that express monoclonal antibodies. The monoclonal antibodies are then screened for reactivity with the immunogen or other desired target cells by methods known in the art, such as an ELISA or Western blotting, to select monoclonal antibodies useful in the present methods.

The antibodies useful in the present invention can be reactive with epitopes specific or unique to ABL proteins that have been conserved in the BCR-ABL and abnormal ABL gene products of the present invention. For example, antibodies reactive with epitopes having sequences within the SH2 region of the normal ABL protein, particularly the B box of this region, are useful in the present methods. Using the method described in Example II, an ABL specific monoclonal antibody, identified herein as 8E9, was produced having a high affinity for such an epitope. The 8E9 monoclonal antibody is in the $IgG_1$ class of antibodies.

A hybridoma cell line producing monoclonal antibody 8E9 was deposited with the American Type Culture Collection (ATCC), 12301 Parklawn Drive, Rockville, Md., 20852, U.S.A. The deposit was made on Jan. 25, 1994 under the provisions of the Budapest Treaty on the International Recognition of the Deposit of Microorganisms for the Purposes of Patent Procedure under Accession No. HB11532.

Relatedly, the present invention also provides purified epitopes within the SH2 region of the normal ABL protein, and particularly within the B box of this region. The SH2 domain encompasses amino acids 125 to 260 of the ABL protein, which is identified in Wang et al., *Cell* 36:349–356 (1984). Purified naturally-occurring epitopes and polypeptides sequences derived from such epitopes can be used as immunogens to generate additional high affinity antibodies useful in the present invention. Such sequences can also be used as probes that are specifically reactive with or hybridize to mRNA associated with BCR-ABL proteins and other $Ph^1$-associated proteins.

The epitopes of the present invention can be identified by testing an anti-ABL antibody, such as 8E9, against a panel of mutant ABL proteins. The mutant ABL proteins can be constructed using recombinant engineering techniques to mutate the normal ABL protein, such as site-directed mutagenesis for example, or by deleting, adding or substituting one or more amino acid sequences. The genetically-engineered ABL mutant proteins can then be expressed in appropriate host cells. Methods for obtaining mutants are well known in the art. According to test results using the 8E9 antibody against ABL mutant proteins, it is believed that 8E9 recognizes an epitope within the amino acids 125–145 of the ABL protein.

As used herein, the term "pure" means that the epitope or polypeptide is substantially free of other biochemical moieties with which it is normally associated in nature. Such purified epitopes and polypeptides can be purified from a native source, synthesized or produced biologically or recombinantly by means known to those skilled in the art.

Methods for detecting the binding of antibody to the reactive components of the sample can be accomplished by any means known in the art. For example, a labeled ligand such as Protein A reactive with a secondary antibody can be used. Alternatively, the primary or secondary antibody can be directly labeled with a detectable marker. Such markers include, for example, radioisotopes, enzymes, fluorogens, chromogens, and chemiluminescent labels.

For the methods of the present invention, radioactive labels are particularly useful. Suitable radioactive labels include tritium, carbon 14, phosphorous 32, iodine 125 or 131, yttrium-90, technetium-99m or sulfur 35. Examples of various suitable radioactive labels are described in U.S. Pat. No. 4,062,733, incorporated herein by reference.

Examples of various enzymatic markers include alkaline phosphatase, horseradish peroxidase, luciferase, β-galactosidase, glucose oxidase, lysozyme, malate dehydrogenase and the like. Suitable substrates for the enzymatic systems include simple chromogens and fluorogens such as, for example, para-nitrophenyl phosphate, β-D-glucose, homovanillic acid, o-dianisidine, bromocresol purple, 4-methyl-umbelliferone and indoxyl phosphate. Chromogenic labels are compounds that absorb light in the visible ultraviolet wavelengths. Such compounds are usually dyes. Fluorogenic compounds emit light in the ultraviolet or visible wavelengths subsequent to irradiation by light or other energy source. A representative listing of suitable fluorogens are described in U.S. Pat. Nos. 4,366,241 and 3,996,345, both of which are incorporated herein by reference. Chemiluminescent labels include, for example, those identified in U.S. Pat. No. 4,104,029, which is incorporated herein by reference.

In the Western blotting procedure, the label can be attached to a second antibody. Polyclonal antibodies are useful as secondary antibodies, particularly those having specificity with the class-determining portion of the primary antibody to increase assay sensitivity.

Depending on the nature of the label or signal-generating system used, a signal can be detected by any appropriate means known in the art. For example, in the case of a radioactive label, X-ray film can be used to develop the signal. For fluorescent labels, a signal can be detected by irradiating with light and observing the level of fluorescence in a fluorometer. For enzyme-catalyzed systems, a color change can be detected visually for a positive reaction when a chromogenic label is used. Further quantification of an enzymatic reaction can be accomplished with a densitometric analysis.

Finally, the present invention also relates to kits containing the antibodies useful in the methods of the present invention. If desired, the kits can also contain ancillary reagents such as an enzyme inhibitor and/or a signal-generating reagent or system. In addition, other ancillary reagents can be included in the kits, for example, buffers, stabilizers and the like.

The following examples are intended to illustrate but not limit the present invention.

EXAMPLE I

Cultured Cell Lines

The cells identified in Table 1 were grown in RPMI medium with 10% fetal calf serum. Normal white blood cells were drawn from volunteers through the leukopheresis unit of the Department of Hematology, MD Anderson Cancer Center, University of Texas. Patient samples were obtained either from the leukopheresis unit (62%), or directly from the patient (38%). Generally, small amounts of blood samples (9–10 ml) were sufficient for the assays.

TABLE 1

| | Cultured Cell Lines | |
|---|---|---|
| Cell Line | P21 BCR-ABL | Source |
| K562 | + | ATCC No. CCL 243 |
| HL-60 | − | ATCC No. CCL 240 |
| SMS-SB | − | Smith et al., J. Immunol. 126:596–602 (1981) |

+ = protein present
− = protein lacking

EXAMPLE II

Production of Anti-ABL Antibody

A monoclonal antibody prepared against an ABL fusion protein expressed in bacteria was used in these studies. Balb/c mice were immunized with the t-ABL fusion protein identified in Wang & Baltimore, *J. Bio.*

*Chem.*, 260:65–71 (1985), which is incorporated herein by reference. The t-ABL fusion protein was purified by expression in a bacteria. Standard fusion techniques were carried out to produce hybridomas according to the procedure of Kohler & Milstein, *Nature* 256:495–497 (1975) as modified by Gerhard, *Monoclonal Antibodies* 370–371 (Plenum Press 1980). Briefly, $10^8$ splenocytes from the immunized mice were fused with $2.5 \times 10^7$ cells of a myeloma cell line in 1.0 ml of 35% polyethylene glycol (PEG 1500). The fused cells were cultured in medium containing hypoxanthine, aminopterin and thymidine (HAT) at 37° in a humidified 5% $CO_2$ incubator.

Three-hundred hybridomas were screened for the production of anti-ABL using microtiter wells coated with the purified t-ABL immunogen. Of the three hundred hybridomas screened, ten were reactive with the immunogen. Hybridoma clone 8E9 was selected because it produced an anti-ABL antibody with the highest apparent affinity in ELISA and 2–3 fold greater intensity in Western immunoblotting tests. The 8E9 antibody is of the murine $IgG_1$ subtype. Large-scale antibody preparation was performed from ascites fluid by ammonium sulfate precipitation followed by DEAE-cellulose chromatography according to methods well known in the art.

The 8E9 antibody recognizes an epitope in the B box of the SH2 domain of the c-ABL and the v-ABL protein. Although the 8E9 antibody was produced using mouse ABL protein as an immunogen, it reacts with ABL proteins from human and monkey cells efficiently. The antibody was adjusted to a concentration of 5.7 mg/ml in phosphate buffered saline solution (PBS). White blood cells from blood, bone marrow, or processed previously by leukopheresis were processed in buffers containing protease inhibitors including 100 KIU/ml Trasylol™ (FBA Pharmaceuticals, New York, N.Y.), 3 mM phenylmethylsulfonyl fluoride (PMSF) and 5 mM benzamidine. Granulocyte and lymphocyte fractions were isolated by gradient fractionation at room temperature using Mono-Poly Resolving Medium (Flow Laboratories, McLean, Va.). Contaminating red cells were removed by two cycles of hypotonic shock in 0.20% NaCl. Except for five samples (PS 18, 25, 27–29), all patient sample cells were treated with 5 mM DIFP for 30 min. on ice. However, the use of DIFP does not appear to be required for P210 BCR-ABL detection, although it may be necessary for long-term storage of samples.

EXAMPLE III

Western Blotting

For Western blotting, cells were lysed in boiling SDS sample buffer composed of 1% sodium dodecyl sulfate (SDS), and 10% 2-mercaptoethanol (2-MEO) containing Tris buffer, pH 8, EDTA, bromophenol blue and glycerol as described. After boiling for 5–7 min, the lysate was clarified by centrifugation for 30–60 min in the Beckman L8-M ultracentrifuge at 40,000 rev/min in a Beckman 50 Ti angle rotor at 25° C. Lysates from $10^7$ cells were applied to 6.5% gels of polyacrylamide.

After electrophoresis, the gel was electroblotted at 4° C. in 192 mM glycine, 25 mM Tris, pH 7.5 and 10% methanol for 2 hrs or overnight at 2 amps onto 0.2 micron cellulose nitrate filters, or in later experiments, Immobilon-P (Millipore, Bedford, Mass.). Filters were prepared for blotting by washing in 3% BSA for 6 hrs at 4° C.

The appropriate antibody dilution depends on the concentration and affinity for the target antigen. Those skilled in the art can readily determine the appropriate dilution based on these factors. The 8E9 antibody was diluted 1:3000 and added to the lysate filters.

After reaction with a 1:3000 dilution of 8E9 antibody overnight at 4° C., and subsequently washing with TN buffer (50 mM Tris-HCl, 150 mM NaCl, 0.2% NP-40 and 0.02% sodium azide, pH 7.5) four times for 15 min (the last wash was performed without NP-40), the antibody-bound to protein bands was detected by [$^{125}$I]-Protein A (Amersham Co., Arlington Heights, Ill.) mixed with rabbit anti-mouse IgG (1 μg per 10 μCi of radioactive Protein A) for 1 hr. A total of 10 μCi of [$^{125}$I]-Protein A/anti-IgG was diluted in 10–15 ml of TN buffer containing 3% BSA. This solution was used no more than three times for detection of ABL-related proteins on two 5×3 inch filters in small trays. Filters were then washed 6 times, the first 5 times with TN buffer containing 0.2% NP-40 detergent and the final wash in only TN buffer and air-dried before exposure to X-ray film (XAR-5).

EXAMPLE IV

Detection of P210 BCR-ABL and P145 ABL in Cell Lines

Figure 1:
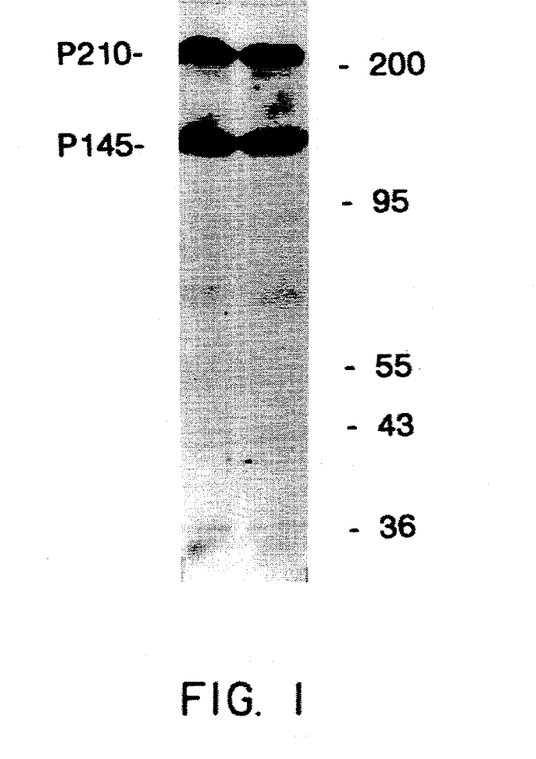
FIG. 1 shows the results of the detection of P210 BCR-ABL and P145 ABL by Western blotting of K562 cell extracts.

Cells expressing P210 BCR-ABL (K562 cells), those lacking the BCR-ABL protein (HL-60 and SMS-SB cells) and normal white blood cells were lysed in boiling SDS sample buffer at a concentration of $10^6$–$10^7$ cells/60 μl and subjected to Western blotting according to the procedure of Example III. The ABL monoclonal antibody 8E9 detected two major bands in K562 cells in about equal amounts with the mobilities of P210 BCR-ABL and P145 ABL as shown in FIG. 1.

Figure 2:
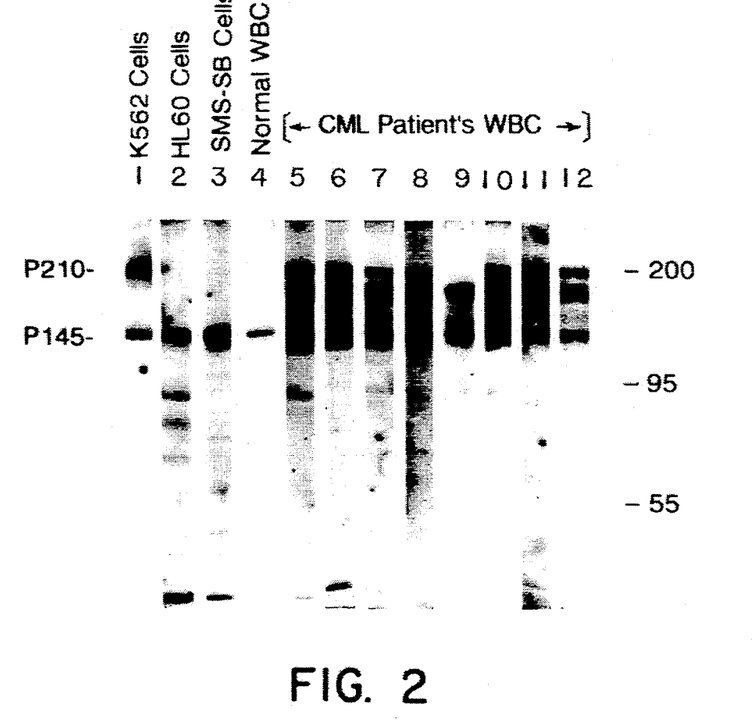
FIG. 2 shows the detection of P210 BCR-ABL and P145 by Western blotting of various $Ph^1$-positive and -negative cell lines, normal white blood cells and patient samples.

Ph$^1$-negative HL-60 and SMS-SB cells contained a major band of P145 ABL and lacked the BCR-ABL protein as shown in FIG. 2. Normal white blood cells also contained only P145 ABL, as expected. In contrast to normal cells, cells from chronic-phase patients contained a major band of P210 BCR-ABL in addition to P145 ABL. As a control, blots were exposed to the [$^{125}$I]-Protein A-rabbit anti-mouse IgG in the absence of the anti-ABL monoclonal antibody. No bands were detected in any of the control extracts tested. In contrast to normal cells, cells from chronic-phase patients contained a major band of P210 BCR-ABL in addition to P145 ABL as shown in FIG. 2.

EXAMPLE V

Detection of BCR-ABL Protein in Blood Cells of Chronic-Phase CML Patients

More than 25 blood samples from 19 chronic-phase CML patients were collected to determine the utility of the Western blotting assay for detection of P210 BCR-ABL in early stages of the disease. The analyses detected bands with the mobility of P210 BCR-ABL and P145 ABL in most of the samples tested as shown in FIG. 2. Variable amounts of lower molecular weight proteins were usually detected in all samples, regardless of their origin.

The abbreviations used herein and in Table 3 below are identified in Table 2. Table 3 summarizes the samples studied to date, and lists important clinical data for each patient.

TABLE 2

| | Abbreviations |
|---|---|
| A | accelerated phase of CML |
| B | blast crisis phase of CML |
| C | chronic phase of CML |
| F | female |
| L | leukopheresis |
| M | male |
| P | peripheral blood sample |
| ALL | acute lymphoblastic leukemia |
| BC | blast cells |
| BM | bone marrow |
| CML | chronic myelogenous leukemia |
| NI | no information |
| WBC | white blood cell |

TABLE 3

Clinical Characterization of CML Patient Samples

| Patient Sample | Age/Sex | Phase of CML | % $Ph^1$ | % BC | WBC ($\times 10^3/\mu l$) | Sample Source | Gene Products P210 | Gene Products P145 | P210 + P190 / P145 |
|---|---|---|---|---|---|---|---|---|---|
| 1 | 43/M | C | 100 | 0 | 113.8 | P. L | + | + | 1.10 |
| 2 | 56/F | A | 100 | 15 | 28.0 | P. L | + | + | 1.38 |
| 3 | 28/M | C | 100 | 2 | 95.6 | P. L | + | + | 1.35 |
| 4 | 39/M | C | 100 | 35* | NI | BM | + | + | 1.55 |
| 5** | 50/M | C | 100 | 5 | 160.6 | P. L | + (P190) | + | 0.92 |
| 6** | 50/M | C | 100 | 0 | 34.4 | P. | + (P190) | + | 3.98 |
| 7** | 50/M | C | 100 | 3 | 19.2 | P. | + (P190) | + | 1.27 |
| 8 | 38/M | B | 100 | 35* | 7.5 | P. | + | + | 2.99 |
| 9 | 22/M | C | 100 | 5 | 118.8 | P. L | + | + | 1.90 |
| 10 | 44/M | C | 100 | 0 | 260.0 | P. L | + | + | 1.84 |
| 11 | 33/M | C | 100 | 1 | 216.0 | P. L | + | + | 2.05 |
| 12 | 57/M | B | 100 | 68 | 38.8 | P. | + | + | 2.93 |
| 13 | 77/M | C | 92 | 0 | 15.7 | P. L | + | + | 1.09 |
| 14 | 31/M | C | 100 | 0 | 57.9 | P. L | + | + | 2.25 |
| 15 | 35/M | C | 100 | 1 | 67.6 | P. L | + | + | 1.13 |
| 16 | 37/M | C | 96 | 0 | 30.0 | P. L | + | + | 1.11 |
| 17 | 25/M | C | 100 | 2 | 88.2 | P. L | + | + | 1.50 |
| 18 | 56/F | C | 100 | 0 | 28.5 | P. | + | + | 1.79 |
| 19*** | 64/M | C | 100 | 4 | 77.2 | P. L | + | + | 1.20 |
| 20*** | 65/M | C | 100 | 1 | 22.1 | P. | + | + | 1.26 |
| 21 | 37/F | C | 100 | 1 | 19.6 | P. L | + | + | 3.03 |
| 22 | 68/M | C | 100 | 0 | 72.5 | P. L | + | + | 1.92 |
| 23 | 48/M | C | 100 | 0 | 10.7 | P. L | + | + | 0.46 |
| 24 | 40/F | C | 100 | 0 | 87.4 | P. L | + | + | 0.68 |
| 25 | 46/MB | (lymphoid) | 100 | 32.8 | 95.0 | P. | + | + | 3.14 |
| 26 | 37/M | C | 100 | 0 | 20.9 | P. L | + | + | 1.34 |
| 27 | 54/F | B | 100 | 88 | 11.2 | P. | + | + | 6.40 |
| 28 | 29/M | ALL (Blast) | 0 | 95 | 185.4 | P. | − | + | |
| 29 | 68/M | C | 100 | 0 | 10.9 | P. | − | + | |

Figure 3:
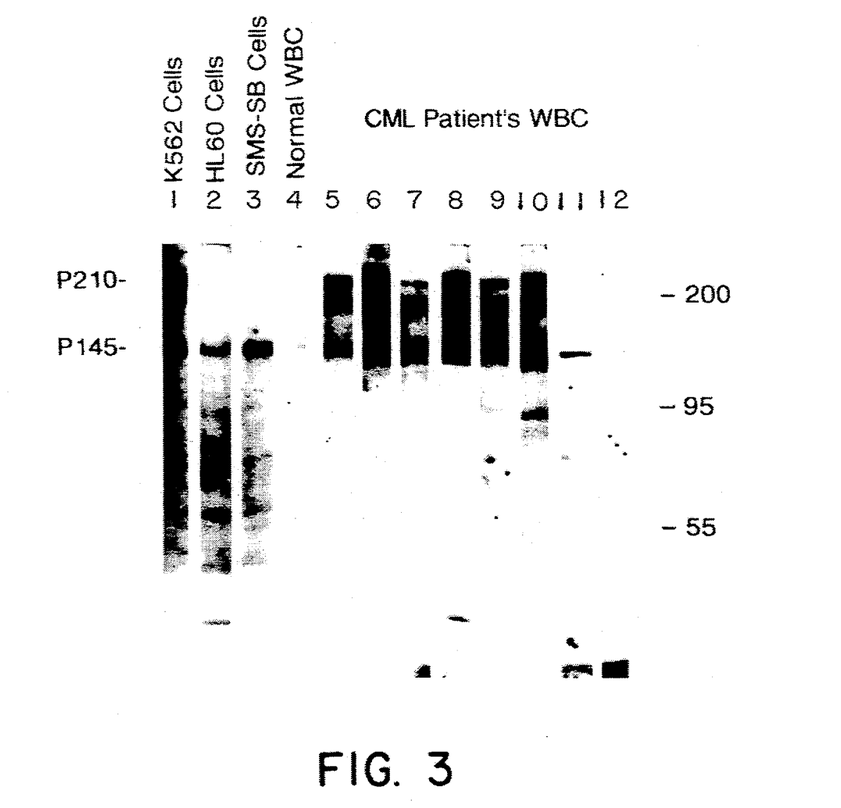
FIG. 3 shows additional results of Western blotting of various cell lines, normal white blood cells and patient samples.

*Blast cells in bone marrow; Three samples of the same patient were taken on different dates; *Two samples from another patient were taken at different dates Nineteen patients were classified as chronic phase, one in accelerated phase, four in blast crisis, and one diagnosed as having $Ph^1$-negative ALL. No significant correlations were apparent regarding whether therapy (pretreatment) was administered to the patient, and the age, sex or white blood cell count of the patient. Most of the samples were processed by leukopheresis prior to subsequent purification to completely remove red blood cells. For analysis of blood samples taken directly from patients, typically less than 10 ml of blood was required to do blotting analyses. Except for one patient sample that lacked detectable BCR-ABL (Table 3, PS 29) and one that contained a P190 ABL band (Table 3, PS 5-7), all other chronic-phase patients contained P210 BCR-ABL, and most contained one to two bands of about 190-kDa (P190 ABL). The $Ph^1$-negative ALL patient (Table 3, PS 28) lacked a BCR-ABL protein, which provides additional validation for the methods of the present invention (FIG. 3, lane 11).

Patient samples 5, 6, and 7 of Table 3, drawn from the same patient on three separate occasions, lacked detectable P210 BCR-ABL and contained only P190 ABL. A single band at P145 was also detected in these samples. Normal white blood cell preparations lacked P190 ABL, and contained only P145 ABL as expected.

Two blast crisis patients were also found to contain P210 BCR-ABL and P145 ABL as well as the P190 ABL. Of interest, the ratio of P210 to P145 in two of four blast crisis patients was similar to that seen in most chronic-phase patients whereas two other blast crisis patients had increased amounts of P210 relative to P145.

One $Ph^1$-positive CML patient in the chronic-phase lacked detectable BCR-ABL proteins but contained P145 ABL (Table 3, PS 29). Although lacking a detectable BCR-ABL protein, this patient was found to possess a BCR-ABL transcript. This RNA contained the 3' bcr exon joined to the second exon of ABL. Thus, unless selective degradation of the BCR-ABL protein occurred, it appears that this transcript is not translated into P210 BCR-ABL in this patient. Several additional patient samples not described in this study were found to lack both P210 BCR-ABL and P145 ABL. Since normal blood samples routinely express the normal ABL protein, the lack of P145 ABL in any assay is indicative of protein degradation during sample processing. In our studies to date, this has been an infrequent occurrence.

EXAMPLE VI Quantitation of $Ph^1$-positive Cells

Figure 4:
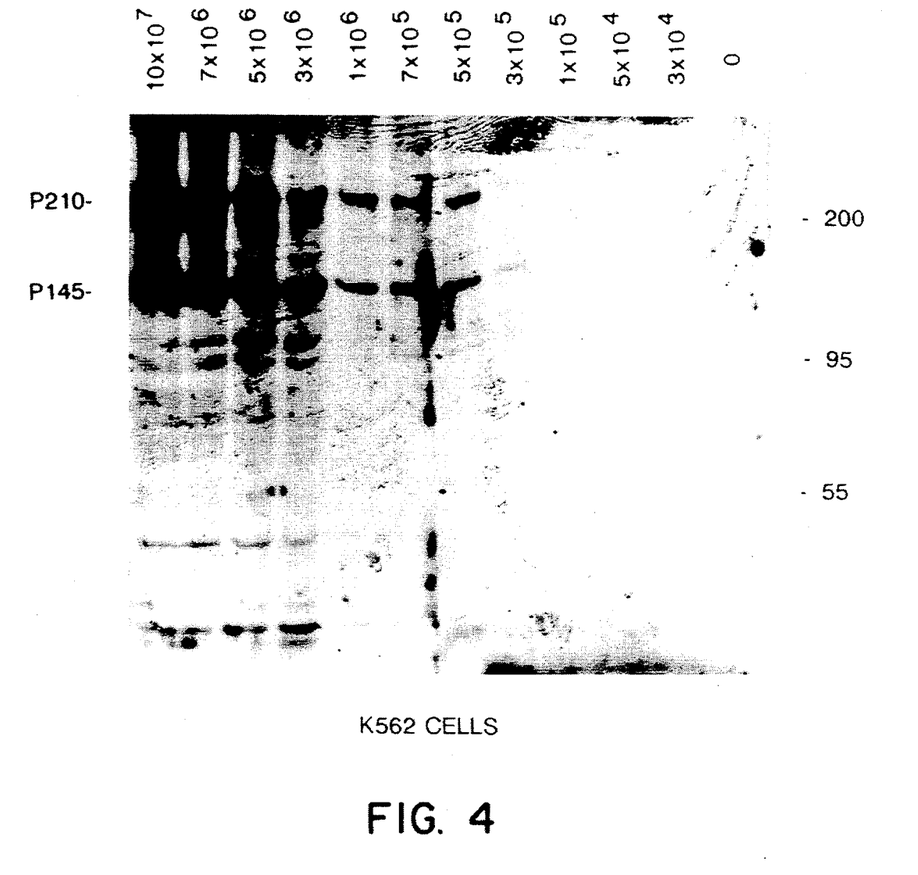
FIG. 4 shows the relative intensity of the bands at various concentrations of K562 cell extracts.

In an attempt to determine whether the Western blotting assay could be used to quantitate the amount of the BCR-ABL protein, experiments were conducted to relate the intensity of the BCR-ABL band to the number of K562 cells analyzed. In this type of experiment, increasing numbers of K562 cells were analyzed and measured to determine the relative intensities of the P210 and P145 bands. The assay detected the BCR-ABL protein in $1 \times 10^5$ K562 cells (using longer exposures). A plot of the band intensities measured as counts per min (cpm) expressed as the ratio of background cpm (Bc) to sample cpm (B) showed a linear relationship between the band intensity of either P210 or P145 and the number of K562 cells as shown in FIG. 4.

EXAMPLE VII

Determination of Tumor Burden

Figure 5:
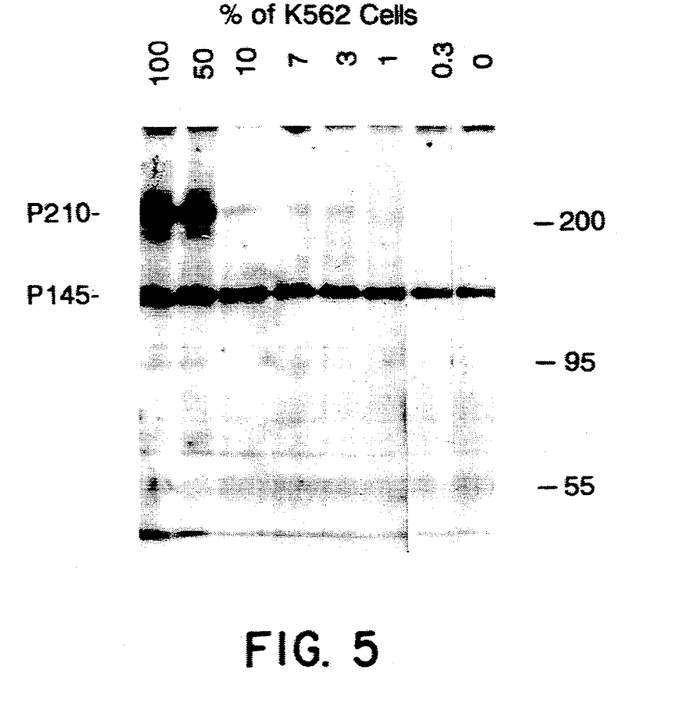
FIG. 5 shows the P210/P145 ratio in various mixtures of K562/SMS-SB cells.
Figure 6:
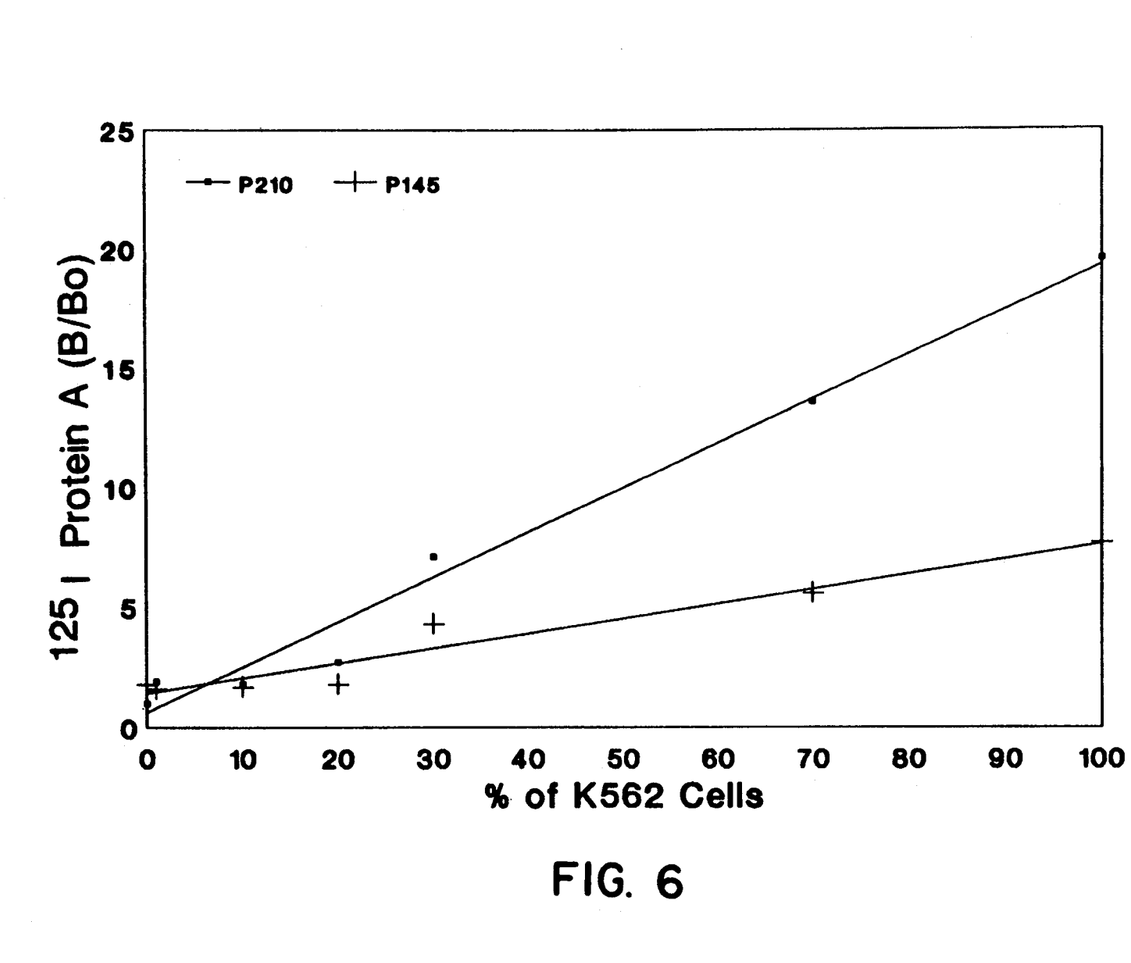
FIG. 6 shows the linear relationship between the amount of P210 BCR-ABL or P145 ABL and increasing percentage of K562 cells in mixtures of SMS-SB cells.
Figure 7:
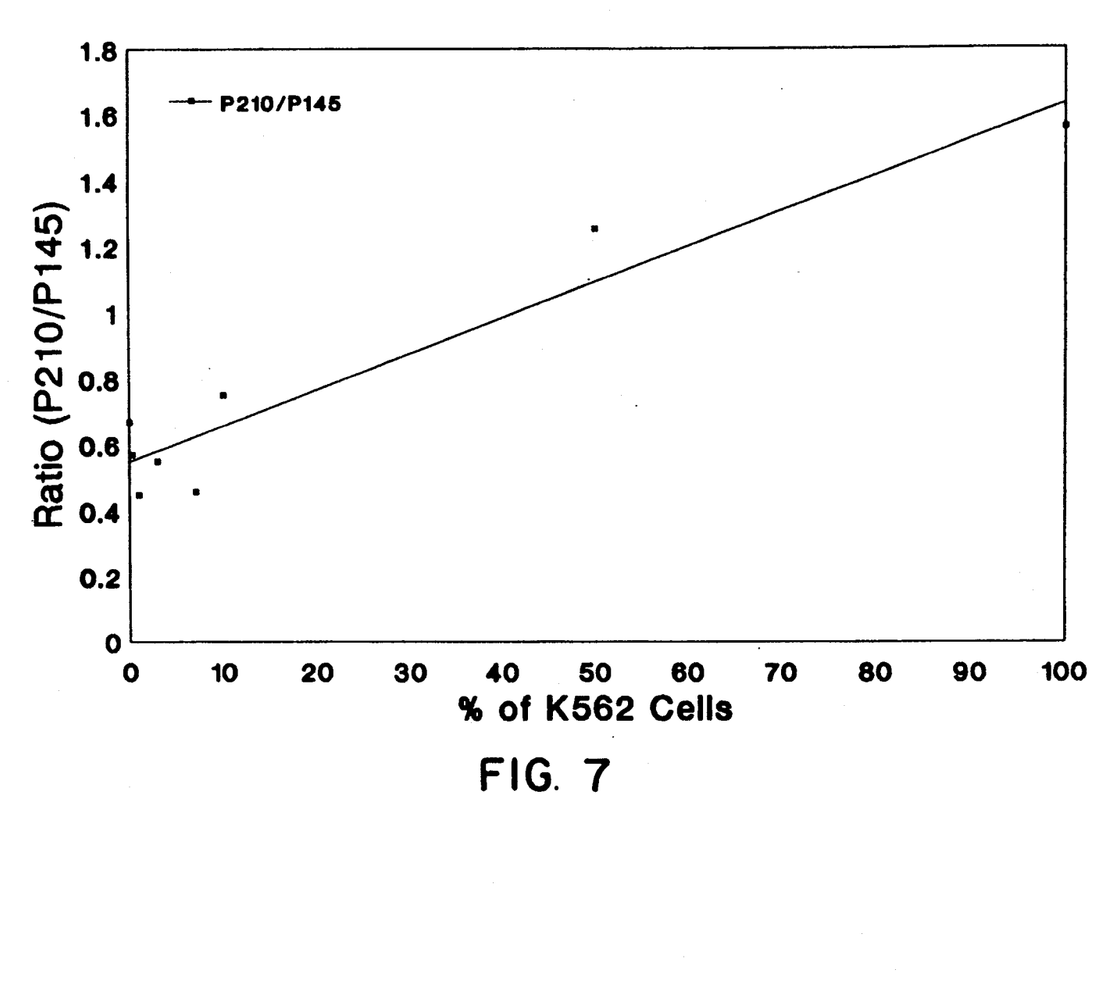
FIG. 7 shows the linear relationship between the ratio of P210/P145 and percentage of K562 cells in mixtures of SMS-SB cells.

Because the 8E9 anti-ABL antibody was able to detect both P210 BCR-ABL and P145 ABL within the same sample and because P210 BCR-ABL is unique to Ph[1]-positive cells, mixtures of BCR-ABL expressing K562 cells and Ph[1]-negative SMS-SB cells prepared in different ratios were assayed to determine whether they would give correspondingly different ratios of P210/P145. The results, shown in FIGS. 5 and 6, demonstrate that the intensity of the P210 BCR-ABL band in the blot is proportional to the percentage of K562 cells in a given cell mixture of Ph[1]-negative cells. Thus, the ratio of P210 and P145 can be used to estimate the number of Ph[1]-positive cells in a given blood sample as shown in FIG. 7.

In this experiment, mixtures composed of 3% K562 cells scored positive for P210 BCR-ABL (3-day exposure). Similar results were obtained with mixtures of K562 cells and normal white blood cells or HL-60 cells. Thus, for any sample of patient white blood cells in which $10^7$ cells are analyzed, the ratio of P210 to P145 will reflect the percentage of Ph[1]-positive cells in the blood sample. These studies indicate that P210 BCR-ABL can be detected in prepared mixtures of normal white blood cells in a total of $10^7$ cells containing as few as 10% Ph[1]-positive chronic-phase CML cells (Table 3, PS 1) in gels exposed for 4 days. Longer exposures will increase the sensitivity even further.

The band intensities of P210/P190 BCR-ABL to P145 ABL from patients in chronic phase and those in blast crisis were compared. The autoradiograms of the blots from 4 blast crisis and 19 chronic-phase patients were scanned with a laser scanning densitometer (Zenith Co., Fullerton, Calif.). The ratio of P210 plus P190 to P145 was larger than 2.5 (range, 2.9 to 6.4) in 4 blast crisis patients and in K562 cells (derived from a blast crisis patient), whereas the ratio ranged from 0.5 to 2.3 in 18 chronic-phase patients (Table 3). In all patients evaluated, the percentage of cells possessing the Ph[1] was between 92 and 100%, indicating that WBC uniformly possess the BCR-ABL gene. The results of the earlier studies discussed immediately above have shown that prepared mixtures of Ph[1]-positive and negative cells show a linear correlation between the ratio of P210 BCR-ABL to P145 ABL and the percentage of Ph[1]-positive cells. These results suggest that P210 BCR-ABL expression is increased in leukemic cells from blast crisis patients compared to those in chronic phase.

The foregoing description of the invention is exemplary for purposes of illustration and explanation. It will be apparent to those skilled in the art that changes and modifications will be possible without departing from the spirit and scope of the invention. It is intended that the following claims be interpreted to embrace all such changes and modifications.

We claim:

1. A method for detecting the presence or absence of a BCR-ABL or abnormal ABL gene product in a patient sample selected from whole blood, bone marrow, plasma or solid tumor, said method comprising:
   (a) denaturing degradative enzymes present in said sample;
   (b) separating said gene products in said sample by molecular weight;
   (c) contacting said separated gene products with a monoclonal antibody that specifically binds with the BCR-ABL gene product and abnormal gene product, but does not cross-react with non-ABL components in said sample, wherein said monoclonal antibody specifically binds the SH2 region of the ABL gene product; and
   (d) detecting the binding of said antibody to said sample, whereby antibody binding to said sample indicates the present of said BCR-ABL or abnormal ABL gene product in said sample.

2. The method of claim 1, wherein the binding of said antibody to said sample is determined by Western blotting.

3. The method of claim 1, wherein step (a) is accomplished by heating said sample to a temperature sufficient to denature said enzymes without significantly degrading peptide bonds of said gene product.

4. The method of claim 3, wherein said sample is treated with an enzyme inhibitor prior to heating.

5. The method of claim 4, wherein said enzyme inhibitor is "Trasylol ™", phenylmethylsulfonyl fluoride (PMSF), benzamidine, diisopropylfluorophosphate (DIFP), leupeptin, pepstatin, EDTA or EGTA.

6. The method of claim 2, wherein said BCR-ABL gene product has an apparent molecular weight in the range of about 190–210 kDa.

7. The method of claim 6, wherein said BCR-ABL gene product has an apparent molecular weight of about 210 kDa.

8. The method of claim 2, wherein the presence of said BCR-ABL or abnormal ABL gene product is associated with the presence of CML in the patient from whom the sample was obtained.

9. A method for the quantitative determination of a BCR-ABL gene product, an abnormal ABL gene product or a normal ABL gene product in a patient sample selected from whole blood, bone marrow, plasma or solid tumor, said method comprising:
   (a) denaturing degradative enzymes present in said sample;
   (b) separating said gene products in said sample by molecular weight;
   (c) contacting said separated gene products with a monoclonal antibody that specifically binds with said BCD-ABL gene product and abnormal gene product, but does not cross-react with non-ABL components in said sample, wherein said monoclonal antibody specifically binds the SH2 region of the ABL gene product; and
   (d) detecting and determining the amount of antibody binding to said BCR-ABL gene product, abnormal gene product or normal ABL gene product, whereby the amount of antibody binding to said BCR-ABL gene product, abnormal gene product or normal ABL gene product indicates the quantity of said BCR-ABL, abnormal ABL gene product or normal ABL gene product, in said sample.

10. The method of claim 9, wherein the binding of said antibody to the sample is determined by Western blotting.

11. The method of claim 9, wherein step (a) is accomplished by heating said sample to a temperature sufficient to denature said degradative enzymes without significantly degrading peptide bonds of said gene product.

12. The method of claim 11, wherein said sample is treated with an enzyme inhibitor prior to heating.

13. The method of claim 9, further comprising the step of relating the amount of said BCR-ABL gene product, abnormal ABL gene product or a combination thereof to a phase of a Ph[1]-positive leukemia.

14. A method for determining a relative amount of Ph[1]-positive leukemic white blood cells in a patient comprising:
   (a) denaturing degradative enzymes in said sample selected from whole blood or bone marrow;
   (b) separating said gene products in said sample by molecular weight;
   (c) contacting said separated gene products with a monoclonal antibody that specifically binds with said BCR-ABL gene product and abnormal gene product, but does not cross-react with non-ABL components in said sample, wherein said monoclonal antibody specifically binds the SH2 region of the ABL gene product; and
   (d) detecting and determining the amount of antibody binding to said BCR-ABL gene product and normal ABL gene product, whereby a ratio of antibody binding to said BCR-ABL gene product compared with antibody binding to normal ABL gene product indicates an amount of said leukemic white blood cells in said sample relative to normal white blood cells.

15. The method of claim 14, wherein said monoclonal antibody is monoclonal antibody 8E9 and antibody binding to said abnormal ABL gene product is further determined in step (d), whereby a ratio of antibody binding to said BCR-ABL gene product and said abnormal ABL gene product compared with antibody binding to said normal ABL gene product indicates an amount of leukemic white blood cells in said sample relative to normal white blood cells.

16. The method of claim 14, wherein the amounts of antibody binding are determined by Western blotting.

17. The method of claim 16, wherein the sample contains about 10[7] white blood cells.

18. A kit for determining the presence or amount of a BCR-ABL gene product in a sample comprising a monoclonal antibody that specifically binds to an epitope within the SH2 domain of said BCR-ABL gene product, an enzyme inhibitor capable of denaturing degradative enzymes in a sample and a signal-generating reagent capable of detecting antibody binding.

19. A monoclonal antibody that specifically binds to an epitope within the SH2 region of an ABL gene product, designated 8E9.

20. The method of claim 1, wherein said monoclonal antibody is 8E9.

21. The method of claim 14, wherein said monoclonal antibody is 8E9.

22. The kit of claim 18, wherein the antibody that specifically binds with said BCR-ABL gene product is 8E9.

23. The method of claim 9, wherein said monoclonal antibody is monoclonal antibody 8E9.

24. A method for screening for the presence of a pathology in a patient, wherein said pathology is associated with the presence of Ph[1]-positive leukemic cells in said patient, comprising:
   (a) obtaining a patient sample, said sample selected from whole blood, bone marrow, plasma or solid tumor;
   (b) denaturing degradative enzyme present in said sample;
   (c) isolating BCR-ABL or abnormal gene products in said sample;
   (d) separating said gene products in said sample by molecular weight;
   (e) contacting said separated gene products with a monoclonal antibody which specifically binds the SH2 region of the ABL gene product; and
   (f) detecting the binding of said antibody to said gene products, wherein the presence of antibody binding is associated with the presence of a Ph[1]-positive leukemic pathology in said patient.

25. The method of claim 24, wherein said pathology associated with Ph[1]-positive leukemic cells is chronic myelogeneous leukemia (CML), acute lymphocytic leukemia (ALL) or acute myelogeneous leukemia (AML).

26. The method of claim 24, wherein the binding of said antibody to said gene product in said sample is determined by Western blotting.

27. The method of claim 24, wherein step (b) is accomplished by heating said sample to a temperature sufficient to denature said enzymes without significantly degrading peptide bonds of said gene product.

28. The method of claim 27, wherein said sample is treated with an enzyme inhibitor prior to heating.

29. The method of claim 28, wherein said enzyme inhibitor is "Trasylol ™", phenylmethylsulfonyl fluoride (PMSF), benzamidine, diisopropylfluorophosphate (DIFP), leupeptin, pepstatin, EDTA or EGTA.

30. The method of claim 24, wherein said BCR-ABL gene product has an apparent molecular weight in the range of about 190–210 kDa.

31. The method of claim 24, wherein said BCR-ABL gene product has an apparent molecular weight of about 210 kDa.

32. The method of claim 30, wherein said monoclonal antibody is 8E9.

* * * * *

UNITED STATES PATENT AND TRADEMARK OFFICE
CERTIFICATE OF CORRECTION

PATENT NO. : 5,369,008
DATED : November 29, 1994
INVENTOR(S) : Arlinghaus et al.

It is certified that error appears in the above-indentified patent and that said Letters Patent is hereby corrected as shown below:

In column 9, line 9, please delete "107" and insert therefor --$10^7$--.

Col. 11, In Table 3, under Age/Sex (in PS 25), please delete "46/MB" and insert therefor --46/M--.

In Table 3, under Phase of CML (in PS 25), please insert --B-- before the word "(lymphoid)".

In column 14, line 50, please delete "BCD-ABL" and insert therefor --BCR-ABL--.

In column 16, line 54, please delete "30" and insert therefor --24--.

Signed and Sealed this

Twenty-third Day of January, 1996

Attest:

BRUCE LEHMAN

Attesting Officer                Commissioner of Patents and Trademarks